United States Patent [19]
Swenson
[11] Plant 4,943
[45] Nov. 16, 1982

[54] GRAPEVINE

[76] Inventor: Elmer Swenson, Rte. 2, Box 118, Osceola, Wis. 54020

[21] Appl. No.: 233,686

[22] Filed: Feb. 11, 1981

[51] Int. Cl.[3] ..... A01H 5/03
[52] U.S. Cl. ..... Plt./47
[58] Field of Search ..... Plt./47

*Primary Examiner*—Robert E. Bagwill
*Attorney, Agent, or Firm*—Merchant & Gould

[57] ABSTRACT

A grapevine which exhibits winter hardiness down to −40° F. in northern Wisconsin, producing white table grapes of fine eating quality, and with vigorous vines which are very resistant to mildew.

3 Drawing Figures

1

ORIGIN AND REPRODUCTION

This invention relates to a new and distinct variety of grapevine which was produced by me pursuant to a continuous grape breeding program which I have conducted for several years at my vineyard and nursery located in Polk County, near Osceola, in northern Wisconsin. The present variety is characterized by excellent winter hardiness and usefulness as a table grape, having a fine eating quality, and the vine being vigorous and resistant to mildew.

For approximately 40 years, I have been growing a large number of grapevines at my vineyard located near Osceola in northern Wisconsin, and have been conducting a breeding program with the intent of developing grapevines having the necessary winter hardiness for northern states and also being commercially useful as wine and/or table grapes.

As background information, it is noted that there have been very few desirable commercial grape varieties for growing in the harsh northern climate of northern Minnesota and Wisconsin and similar northern states. Although this northern region has a summer heat thermal accumulation similar to that of the best known grape growing areas of the world, the low winter temperatures in Minnesota, Wisconsin and similar climates have generally prevented development of vineyards in such region because of the lack of suitably hardy grape varieties.

The current vineyard cultural practices in the above-noted northen region of the United States generally involve early fall pruning, after which the vines are removed from trellises and laid upon the ground with covering material for wintering. In the spring, the grapevines are uncovered and re-trellised, all of which involves considerable labor costs, which are generally prohibitive and make it quite difficult for nothern vineyards in such climates to operate profitably. Accordingly, for grapevines to be of significant commercial value to vineyards in northern regions, such as Minnesota and Wisconsin, it has become nearly essential that the varieties be hardy enough to remain upon the trellises throughout the winter months, without removal and winter covering. The present variety has this desirable characteristic.

Accordingly, this new variety of grapevine was selected by me for its combination of excellent winter hardiness and usefulness as a fine quality table grape, with the vine also being vigorous and resistant to mildew.

2

The present variety is the result of my above-noted breeding program in which my varietal selections are designated by number with the prefix ES. This variety is a selected seedling resulting from the open pollination of my earlier variety ES217 (Minnesota 78 × Golden Muscat). I have identified the present variety as ES 1-63 and selected the name "Kay Gray" therefor.

The present variety has been reproduced by means of vine cuttings, and I have carefully observed the variety for several years. My continual observation and testing of this variety has convinced me that it is a new and improved cultivar of grapevine, as indicated by the following unique combination of outstanding qualities which distinguish this variety from all other varieties of grapevine known to me.

SUMMARY OF CHARACTERISTICS

The unique combination of characteristics of the present variety ES 1-63 named "Kay Gray" are as follows:

1. *Winter Hardiness.*—The present variety has excellent winter hardiness for northern states, such as Minnesota and Wisconsin, whereby the vines may remain on trellises throughout the winter without covering. More specifically, this variety has survived on trellises with a winter temperature of −40° Fahrenheit and with no apparent injury to the vines or buds thereon and with no winter covering. The winters of 1977 and 1978 were particularly harsh in northern Wisconsin and provided an excellent field test of the present cultivar, with temperatures reaching −40° F. at my vineyard each year. Such observations and hardiness testing of the present variety have been at my vineyard and nursery located near Osceola, in Polk County, in northern Wisconsin.

2. *Eating Quality.*—This variety has produced grapes of fine table or eating quality, producing white fruit which ripens early mid-season and with many labrusca qualities. The texture of the pulp of the grapes is juicy and slightly crisp, and the slip skin is tender and relatively nonfragile.

3. *Vine Qualities.*—This variety produces vines which are vigorous and very resistant to mildew.

ASEXUAL REPRODUCTION

The present variety has been asexually reproduced by me by means of vine cuttings at my nursery and vineyard in Polk County, near Osceola, Wis. Such asexual reproduction confirms that the characteristics and qualities stated herein for this variety are true to form and consistent through succeeding propagation.

DETAILED DESCRIPTION

The accompanying drawings comprise photographs showing characteristics of this new variety. The photographs were taken of specimens of the variety growing in my above-noted vineyard near Osceola, Wis., and the color photographs depict color features as true as reasonably possible.

FIG. 1 is a color photograph showing the form and growth of a mature vine of the present variety.

FIG. 2 is a color photograph showing typical fruit clusters of the present variety.

FIG. 3 is a color photograph showing the mature summer leaf form for typical leaves of this variety.

The following is a detailed specification of the pomological characteristics of my new variety, with color terminology or references in accordance with the Royal Horticultural Society Color Chart. Where dimensions, sizes, colors and other characteristics are given, it is to be noted that the same are approximations of averages as they appear under conditions prevailing in my vineyard near Osceola, Wis.

Vine:

*Growth habit.*—Trailing growth habit and vigorous.

*Trunk.*—Thick and sheds bark in long strips (Riparia fashion), Brown. Needs support.

*Canes.*—Average length is 3.1 meters. Tendrils have the labrusca characteristic of tendril at every node. Internodes medium in length with an average distance between nodes of 8.0 centimeters.

*Foliage.*—Petiolar sinus of mature leaf tends to be medium to narrow and V-shaped. Lower lateral sinuses not very pronounced. Teeth along leaf margin are sharp and shallow. Leaf has a distinct cupped shape and is slightly wider at maximum width than from leaf tip to base. Mature leaf close to Color Group Green 137A with leaf underside close to Yellow-Green 148B, which creates the illusion of having leaves with "white" undersides.

Grapes: Mature leaf size is approximately 6.5 inches wide and 7.5 inches long.

*Maturity.*—Early mid-season. Late August to mid-September.

*Size of berry.*—1.8 centimeter average with largest berry on clusters approximately 2.0 centimeters.

*Shape of berry.*—Spherical.

*Ripening.*—Similar to Edelweiss. Late August to mid-September.

*Color of berry.*—Close to color group Yellow-Green 145B.

*Cluster weight.*—2.2 oz. average.

*Color of juice.*—Close to color group Green-White 157B.

*Seeds per berry.*—2.1 average.

*Pulp.*—Texture juicy and slightly crisp. The slip skin is tender but not as fragile as the Edelweiss. Color of the pulp is close to Yellow-Green 150D.

*Sugar and acid.*—21.1 percent sugar at 0.85 percent acid. Date tested: Sept. 7, 1980.

*Berries per cluster.*—Approximately thirty-five (35).

Cluster:

*Cluster size.*—Small, compact and cylindrical, usually with one small shoulder. Length of cluster is 8.1 centimeters and a 2.5 centimeter stem.

*Clusters per shoot.*—Usually three.

*Clusters ripening.*—Begins unevenly but full at maturity.

Other: Very resistant to mildew. Appears to be as winter hardy as the Beta. Excellent table grape.

I claim:

1. A new and distinct variety of grapevine, substantially as shown and described herein, characterized particularly as to novelty by the unique combination of winter hardiness down to −40° F. in northern Wisconsin, producing white table grapes of fine eating quality, and with vigorous vines which are resistant to mildew.

* * * * *

FIG. 1
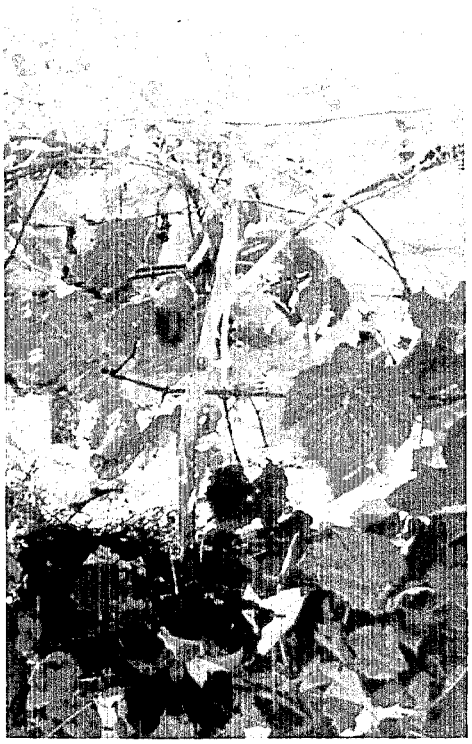
FIG. 2
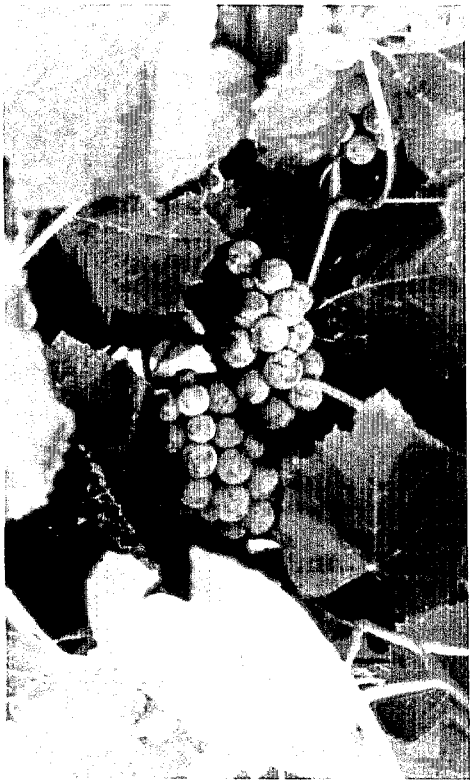
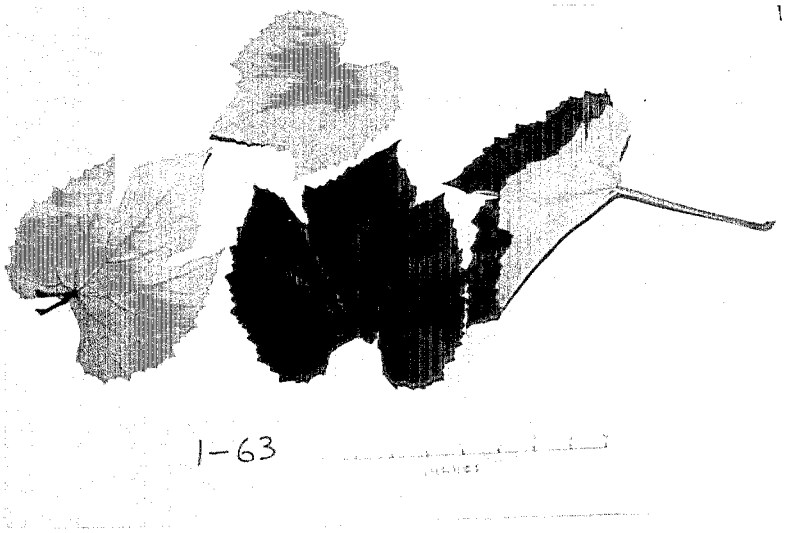
FIG. 3

UNITED STATES PATENT AND TRADEMARK OFFICE

CERTIFICATE OF CORRECTION

PATENT NO. : PP04943

DATED : November 16, 1982

INVENTOR(S) : Elmer Swenson

It is certified that error appears in the above-identified patent and that said Letters Patent is hereby corrected as shown below:

Column 4, lines 2-6 should read:

-- "white" undersides. Mature leaf size is approximately 6.5 inches wide and 7.5 inches long.

Grapes:

Maturity.--Early mid-season. Late August to mid-September.--.

Signed and Sealed this

*Eighth* Day of *March 1983*

[SEAL]

*Attest:*

GERALD J. MOSSINGHOFF

*Attesting Officer*

*Commissioner of Patents and Trademarks*